(12) United States Patent
Kawamura

(10) Patent No.: US 7,282,367 B2
(45) Date of Patent: Oct. 16, 2007

(54) METHOD FOR VERIFYING AMOUNT OF SAMPLE SOLUTION, METHOD FOR CONTROLLING MEASUREMENT SYSTEM AND METHOD FOR MEASURING CONCENTRATION OF SOLUTION IN APPARATUS FOR MEASURING OPTICAL CHARACTERISTIC

(75) Inventor: Tatsurou Kawamura, Kyotanabe (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 768 days.

(21) Appl. No.: 09/820,854

(22) Filed: Mar. 30, 2001

(65) Prior Publication Data

US 2001/0031500 A1    Oct. 18, 2001

(30) Foreign Application Priority Data

Apr. 13, 2000    (JP) .............................. 2000-111731

(51) Int. Cl.
*G01N 21/01*    (2006.01)

(52) U.S. Cl. .................. 436/55; 436/148; 436/164; 422/82.05; 422/82.09

(58) Field of Classification Search .................. 436/55, 436/148, 164, 168, 171, 172; 422/82.05, 422/82.09, 82.11
See application file for complete search history.

(56) References Cited

U.S. PATENT DOCUMENTS

| | | | | |
|---|---|---|---|---|
| 4,065,358 A | * | 12/1977 | Kawai et al. | 435/288.2 |
| 4,372,683 A | * | 2/1983 | Sternberg | 356/338 |
| 4,381,895 A | | 5/1983 | Hughes et al. | |
| 4,436,822 A | * | 3/1984 | Eseifan | 436/164 |
| 4,659,550 A | * | 4/1987 | Schildknecht | 422/73 |
| 4,943,416 A | * | 7/1990 | Kikuchi et al. | 422/63 |
| 5,100,805 A | * | 3/1992 | Ziege et al. | 436/517 |
| 5,104,527 A | | 4/1992 | Clinkenbeard | |
| 5,110,724 A | * | 5/1992 | Hewett | 435/11 |
| 5,236,666 A | * | 8/1993 | Hulette et al. | 422/65 |
| 5,271,902 A | * | 12/1993 | Sakka et al. | 422/100 |
| 5,290,517 A | * | 3/1994 | Samuels et al. | 422/58 |
| 5,298,978 A | * | 3/1994 | Curtis et al. | 356/627 |
| 5,366,897 A | * | 11/1994 | Hager et al. | 436/55 |
| 5,451,525 A | * | 9/1995 | Shenkin et al. | 436/63 |
| 5,601,980 A | * | 2/1997 | Gordon et al. | 435/6 |
| 5,627,522 A | | 5/1997 | Walker et al. | |

(Continued)

FOREIGN PATENT DOCUMENTS

EP    0 805 352    11/1997

OTHER PUBLICATIONS

Partial European Search Report issued in corresponding European Patent Application No. EP 06 12 1652, dated Mar. 8, 2007.

*Primary Examiner*—Brian R. Gordon
(74) *Attorney, Agent, or Firm*—McDermott Will & Emery LLP

(57) ABSTRACT

A verification method of a sample solution amount includes the steps of: detecting at least one of a transmitted light component, a scattered light component and a reflected light component of a light by a photosensor while irradiating a sample solution, which is being injected into a sample cell, with the light; and verifying that a predetermined amount of the sample solution is held in the sample cell based on a change in an output signal from the photosensor.

10 Claims, 10 Drawing Sheets

U.S. PATENT DOCUMENTS

| | | | |
|---|---|---|---|
| 5,646,046 A * | 7/1997 | Fischer et al. | 436/49 |
| 5,730,937 A * | 3/1998 | Pardikes | 422/62 |
| 5,736,103 A * | 4/1998 | Pugh | 422/68.1 |
| 5,811,312 A * | 9/1998 | Hasegawa et al. | 436/527 |
| 5,843,651 A * | 12/1998 | Stimpson et al. | 435/6 |
| 5,871,698 A * | 2/1999 | Laguna et al. | 422/82.05 |
| 5,879,628 A * | 3/1999 | Ridgeway et al. | 422/73 |
| 5,900,152 A * | 5/1999 | Janik et al. | 210/656 |
| 5,965,447 A * | 10/1999 | Sekiyama et al. | 436/49 |
| 6,074,879 A * | 6/2000 | Zelmanovic et al. | 436/10 |
| 6,100,094 A * | 8/2000 | Tajima | 436/54 |
| 6,235,534 B1 * | 5/2001 | Brookes et al. | 436/164 |
| 6,241,947 B1 * | 6/2001 | Komatsu et al. | 422/67 |
| 6,345,528 B2 * | 2/2002 | Petro et al. | 73/61.52 |
| 6,398,956 B1 * | 6/2002 | Coville et al. | 210/321.75 |
| 6,398,961 B1 * | 6/2002 | Wei et al. | 210/634 |
| 6,406,632 B1 * | 6/2002 | Safir et al. | 210/656 |
| 6,565,815 B1 * | 5/2003 | Chang et al. | 422/198 |
| 6,620,622 B1 * | 9/2003 | Kawamura | 436/164 |
| 6,623,700 B1 * | 9/2003 | Horine et al. | 422/100 |
| 6,632,619 B1 * | 10/2003 | Harrison et al. | 435/7.2 |
| 6,635,224 B1 * | 10/2003 | Gui et al. | 422/62 |
| 6,635,491 B1 * | 10/2003 | Khalil et al. | 436/95 |
| 6,652,810 B1 * | 11/2003 | Ziegler | 422/82.08 |
| 6,682,903 B2 * | 1/2004 | Saunders | 435/7.92 |
| 6,706,536 B1 * | 3/2004 | Carroll et al. | 436/164 |
| 6,723,290 B1 * | 4/2004 | Wardlaw | 422/102 |
| 6,740,240 B2 * | 5/2004 | Coville et al. | 210/645 |
| 6,861,034 B1 * | 3/2005 | Elrod et al. | 422/100 |
| 6,900,021 B1 * | 5/2005 | Harrison et al. | 435/7.21 |
| 6,900,059 B1 * | 5/2005 | Shinn et al. | 436/43 |
| 6,924,152 B2 * | 8/2005 | Matsubara et al. | 436/180 |
| 2002/0008032 A1 * | 1/2002 | Hayenga | 204/603 |
| 2002/0031837 A1 * | 3/2002 | Matsubara et al. | 436/180 |
| 2002/0042142 A1 * | 4/2002 | Kawamura | 436/50 |
| 2002/0055178 A1 * | 5/2002 | Wardlaw | 436/165 |
| 2003/0086823 A1 * | 5/2003 | Fernando et al. | 422/81 |
| 2003/0156984 A1 * | 8/2003 | Lemke et al. | 422/58 |
| 2003/0175983 A1 * | 9/2003 | Wei et al. | 436/163 |
| 2004/0147039 A1 * | 7/2004 | Van Der Mark et al. | 436/164 |

\* cited by examiner

Distance from bottom of sample cell to lowermost part of solution surface: d/(mm)

Time elapsed since start of dropping of sample solution: t(s)

Distance from bottom of sample cell to lowermost part of solution surface: d/(mm)

Time elapsed since start of dropping of sample solution: t(s)

F I G. 9
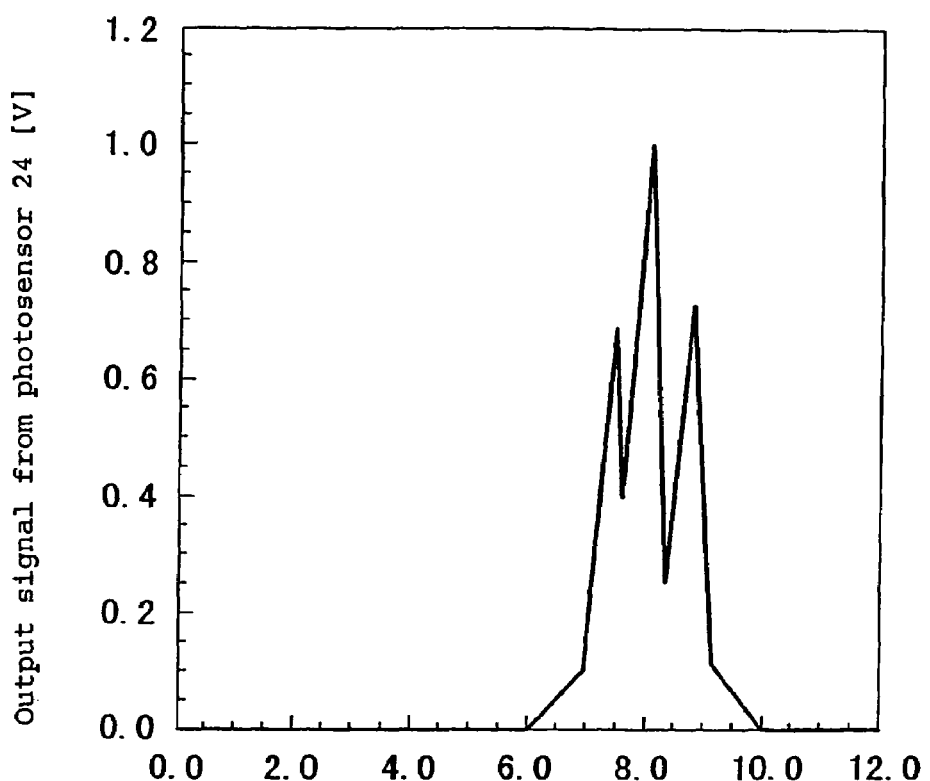
Distance from bottom of sample cell to lowermost part of solution surface: d/(mm)
Time elapsed since start of dropping of sample solution: t/(s)

F I G. 1 0
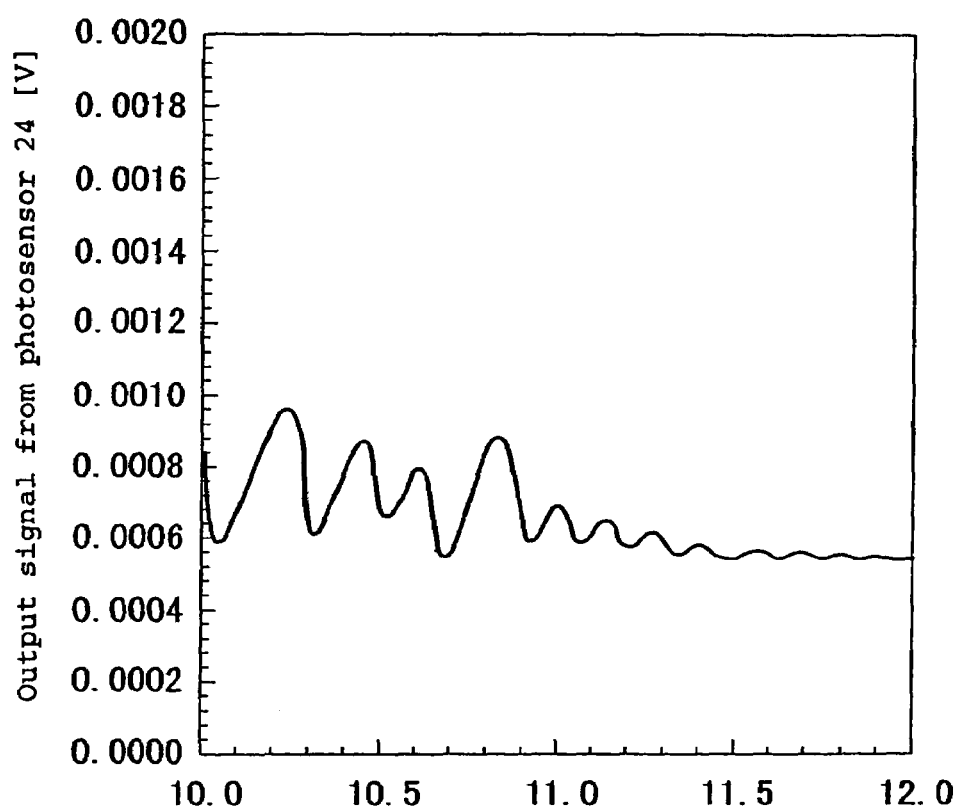
Distance from bottom of sample cell to lowermost part of solution surface: d/(mm)
Time elapsed since start of dropping of sample solution: t/(s)

METHOD FOR VERIFYING AMOUNT OF SAMPLE SOLUTION, METHOD FOR CONTROLLING MEASUREMENT SYSTEM AND METHOD FOR MEASURING CONCENTRATION OF SOLUTION IN APPARATUS FOR MEASURING OPTICAL CHARACTERISTIC

BACKGROUND OF THE INVENTION

The present invention relates to a method for verifying an amount of a sample solution, a method for controlling a measurement system and a method for measuring a concentration of a solution used for measuring an optical characteristic of a sample solution.

More specifically, it relates to a method for verifying that a sample solution is held in a sample cell in an amount required for measurement when the sample solution is supplied into the sample cell. This method is extremely effective particularly when a concentration of the sample solution is measured by injecting a reagent into the sample solution, because it is necessary to fix or control the volume ratio of the sample solution and the reagent.

Further, when the sample solution is a urine, the urine can be directly discharged into the sample cell. Therefore, simplicity and high reliability of urinalysis and compactness and lower price of urinalysis apparatus can be achieved, resulting in high practicability.

In general, when measuring an optical characteristic of a sample solution, the sample solution is held in a sample cell. The sample cell has such structure that a light propagates through the inside of the sample solution held therein. For example, the sample cell is made of a glass or the like which has the shape of a rectangular solid, and the light-transmitting surface thereof is transparent. In order to measure an optical characteristic of the sample solution, it is necessary to supply a predetermined amount of the sample solution into such a sample cell. Normally, this sample cell has an opening at the top, through which the predetermined amount of the sample solution is supplied by a dropper, pipette, syringe or the like.

Further, when a concentration of a specific substance in a sample solution is measured, a predetermined amount of a reagent is mixed with a predetermined amount of the sample solution to fix the volume ratio of the sample solution and the reagent. Then, an optical characteristic of an analyte in the sample solution is measured to determine the concentration thereof. It has hitherto been necessary to supply a predetermined amount of a sample solution into the sample cell in order to fix the volume ratio of the sample solution and the reagent. Therefore, there has been required a step of placing the sample solution in a beaker or the like, and measuring it by a pipette, a syringe or the like to previously determine the volume, and then supplying the sample solution into the sample cell. This step presents not only a problem of complicating the measurement of a concentration of the sample solution, but also that of making an error due to a mistake during the measuring operation more likely to occur.

Further, when the sample solution is a urine, it is necessary to measure the urine once discharged into a cup or the like, and then supplying the predetermined amount of the urine into the sample cell. This also presents another problem that the step is troublesome especially when the urinalysis is carried out at home, causing the user to have a great reluctance.

In view of the above problems in the prior art, it is an object of the present invention to provide a method for verifying that a predetermined amount of a sample solution is held in a sample cell when the sample solution is supplied into the sample cell. More specifically, it is an object of the present invention to provide a method for verifying that a predetermined amount of a urine required for urinalysis is held in a sample cell when the urine discharged into a toilet bowl is received by a container or the sample cell itself in a hollow space of the toilet bowl.

According to this method, the mixing ratio of a sample solution and a reagent can be fixed or controlled by fixing or controlling only an amount of the reagent required for measurement of the sample solution, without previously measuring the amount of the sample solution and supplying it into the sample cell.

Namely, the present invention provides a method for controlling a measurement system that facilitates automation of measurement of a sample solution and enables greater efficiency and labor saving of the measurement and the test, and a method for measuring a concentration of a solution using the same.

BRIEF SUMMARY OF THE INVENTION

In order to solve the above problems, the present invention first provides a method for verifying an amount of a sample solution comprising the steps of: (a) detecting at least one selected from the group consisting of a transmitted light component, a scattered light component and a reflected light component of a light by a photosensor while irradiating a sample solution, which is being injected into a sample cell, with the light; and (b) verifying that a predetermined amount of the sample solution is held in the sample cell based on a change in an output signal from the photosensor. Herein, upon the verification, the injection (inflow) of the sample solution may be suspended.

In other words, the present invention utilizes changes in a transmitted light component, a scattered light component and a reflected light component in response to the fact that the surface of the sample solution being injected into the sample cell rises to traverse a fixed optical path of an irradiated light into the sample solution.

Herein, it is effective that the step (b) is a step of verifying that the predetermined amount of the sample solution is held in the sample cell based on the fact that an absolute value of an amount of change in the output signal over time is maintained at the first predetermined value or less for the first predetermined duration or longer.

Further, it is effective that the step (b) is a step of detecting an inflow of the sample solution into the sample cell based on the fact that the absolute value has become the second predetermined value or greater, followed by verifying that the predetermined amount of the sample solution is held in the sample cell based on the fact that the absolute value of an amount of change in the output signal over time is maintained at the first predetermined value or less for the first predetermined duration or longer, after detecting the inflow.

It is preferable that the second predetermined value is greater than the first predetermined value.

It is also effective that the step (a) is a step of detecting a transmitted light component of a light by a photosensor while irradiating a sample solution, which is being injected into a sample cell, with the light, and the step (b) is a step of verifying that the predetermined amount of the sample solution is held in the sample cell based on the fact that the output signal has become the third predetermined value or greater.

Further, it is effective that the step (a) is a step of detecting a scattered light component of a light by a photosensor while irradiating a sample solution, which is being injected into a sample cell, with the light, and the step (b) is a step of verifying that the predetermined amount of the sample solution is held in the sample cell based on the fact that the output signal has become the fourth predetermined value or less.

When the sample solution is a urine, it is effective that the step (a) is a step of detecting at least one selected from the group consisting of a transmitted light component, a scattered light component and a reflected light component of a light by a photosensor while irradiating a urine, which is being injected into a sample cell provided in a hollow space of a toilet bowl, with the light.

Next, the present invention also provides a method for controlling a measurement system comprising the steps of: (a) detecting at least one selected from the group consisting of a transmitted light component, a scattered light component and a reflected light component of a light by a photosensor while irradiating a sample solution, which is being injected into a sample cell, with the light; (b) verifying that a predetermined amount of the sample solution is held in the sample cell based on a change in an output signal from the photosensor; and then (c) measuring an optical characteristic of the sample solution. Herein, after verifying that the predetermined amount of the sample solution is held in the sample cell, the inflow of the sample solution may be suspended.

This method for controlling a measurement system is a method for controlling a measurement system used for a measurement of an optical characteristic in an optimum condition for the measurement. It is effective that the method further comprises a step of verifying that the sample solution has become stable based on the fact that the absolute value of the amount of change in the output signal over time is maintained at the fifth predetermined value or less for the second predetermined duration or longer, after the step (b) and before the step (c).

It is preferable that the fifth predetermined value is less than the second predetermined value.

It is also effective that the irradiated light in the step (a) is also used for measuring the optical characteristic in the step (c).

Further, the sample solution may be transfused from the sample cell to another sample cell after the step (b), and the rest of the steps may be conducted thereafter. In this case, the former sample cell is used only for trapping the predetermined amount of the sample solution, and the rest of the steps, such as a measurement of an optical characteristic, are conducted in the latter sample cell.

In the above method for controlling a measurement system, the step (c) may be a step of detecting a light, which has been transmitted through the sample solution and an analyzer, by a photosensor to measure an angle of rotation of the sample solution, using the output signal from the photosensor as a transmitted light component.

The method may further comprise the steps of: (d) discharging the sample solution from the sample cell after the step (c); and then (e) washing the sample cell.

Further, it is effective that the steps (d) and (e) are conducted simultaneously by replacing the sample solution in the sample cell with a cleaning solution.

Further, when the sample solution is a urine, it is effective that the steps (a) to (c) are conducted after the sample cell installed in a position closed to a side wall of a toilet bowl is moved into a hollow space of the toilet bowl, and the rest of the steps are conducted after the sample cell is restored to the initial (original) position.

When the sample solution is a urine, it is also effective that the steps (a) and (b) are conducted after the sample cell installed in a position closed to a side wall of a toilet bowl is moved into a hollow space of the toilet bowl, and the rest of the steps are conducted after the sample cell is restored to the initial position.

It is preferable that the urine and/or the cleaning solution are discharged into the toilet bowl.

Further, the present invention also provides a method for measuring a concentration of a solution comprising the steps of: (a) detecting at least one selected from the group consisting of a transmitted light component, a scattered light component and a reflected light component of a light by a photosensor while irradiating a sample solution, which is being injected into a sample cell, with the light; (b) verifying that a predetermined amount of the sample solution is held in the sample cell based on a change in an output signal from the photosensor; (c) measuring an optical characteristic of the sample solution after mixing therewith a predetermined amount of a reagent with the sample solution, followed by measuring a concentration of a specific substance contained in the sample solution.

It is preferable that the step (c) is a step of measuring an angle of rotation of the sample cell to measure a concentration of an optically active substance contained in the sample solution, followed by measuring a concentration of a specific substance contained in the sample solution by measuring an optical characteristic of the sample solution after mixing thereto a predetermined amount of a reagent.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 9 is a graph showing the relation between the output signal from the photosensor and the distance from the bottom of the sample cell to the lowermost part of the solution surface or the elapsed time since the start of the dropping of the sample solution in Example 6 of the present invention.

FIG. 10 is a partial enlarged view of FIG. 9 showing the value of the output signal from the photosensor 8 at around 0 V, when d=10 to 12.

DETAILED DESCRIPTION OF THE INVENTION

As discussed above, the present invention relates to a method for verifying an amount of a sample solution, and a method for controlling a measurement system and method for measuring a concentration of a solution using the same. Therefore, the method for verifying an amount of a sample solution in accordance with the present invention will be described first.

Figure 1:
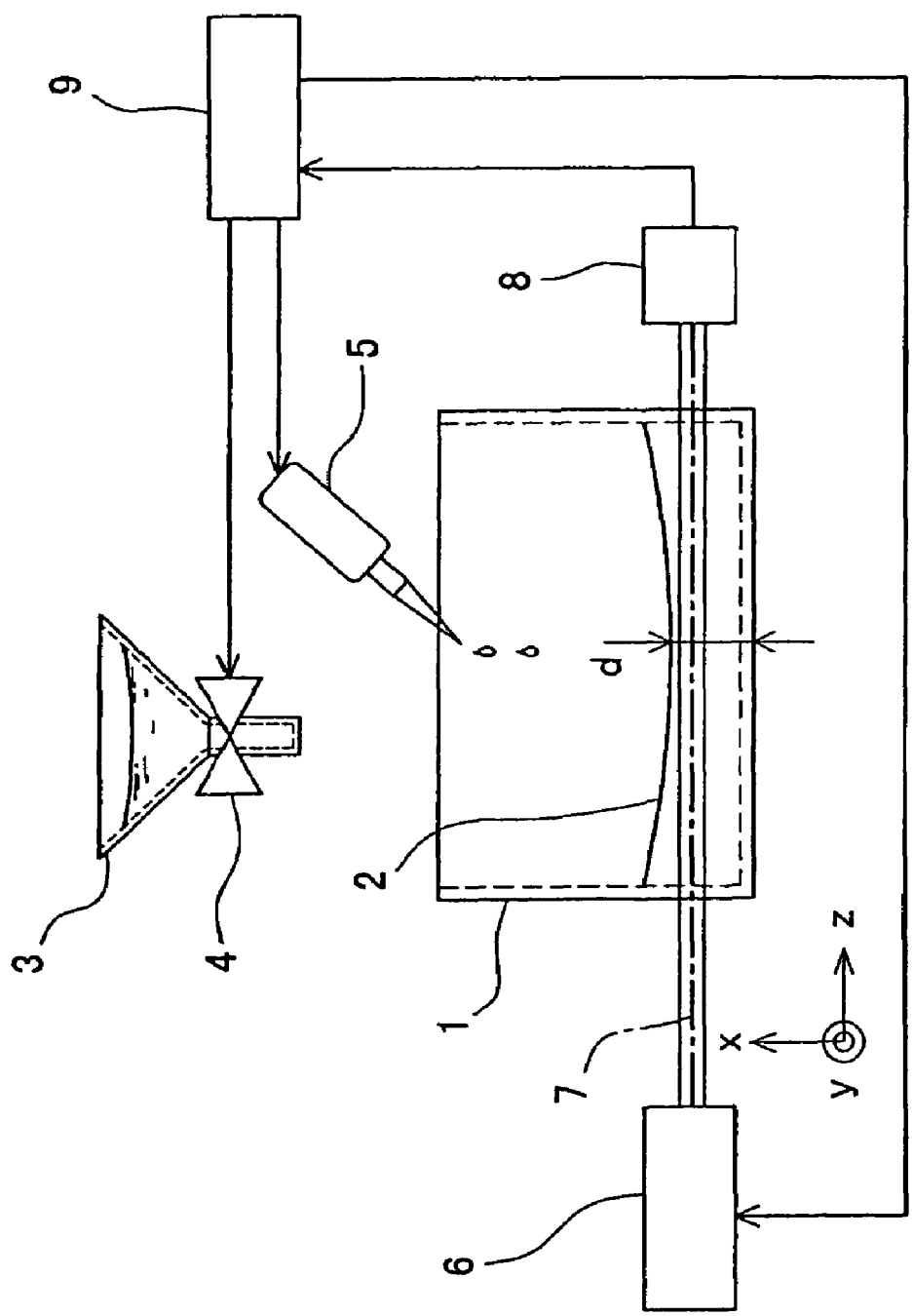
FIG. 1 is a view showing the configuration of the apparatus for measuring an optical characteristic used in Example 1 of the present invention.

As a result of diligent studies on the relation between a level of a sample solution in a sample cell and an optical power propagating through the sample solution by using the apparatus for measuring an optical characteristic shown in FIG. 1, the present inventor has accomplished the method for verifying an amount of a sample solution in accordance with the present invention.

First, such measurement will be described below in detail with reference to FIG. 1. FIG. 1 is a view showing the configuration of an apparatus for measuring an optical characteristic in accordance with the present invention.

In FIG. 1, a skeleton of a sample cell 1 of the present invention is a container made of aluminum which has the shape of a rectangular solid, an opening at the top and a glass plate as an optical window embedded on both ends of the optical path (not shown), so that the container allows a light to transmit through a sample solution while holding the sample solution therein. The distance from the lowermost part of a surface 2 of the sample solution to the bottom of the sample cell 1 is indicated with "d". The distance of the long axis of the sample cell, that is, the distance between the optical windows is 50 mm, the distance of the short axis is 10 mm, and the propagating distance in the sample solution is 50 mm. The apparatus for measuring an optical characteristic shown in FIG. 1 comprises a funnel 3 for temporarily trapping the sample solution, an electromagnetic valve 4 for controlling the dropping of the sample solution trapped in the funnel 3 into the sample cell 1, and a pipette 5 for injecting a predetermined amount of a reagent into the sample solution. A semiconductor laser module as a light source 6 projects a substantially parallel light 7, which has the shape of a circle, a wavelength of 670 nm, an intensity of 3.0 mW and a beam radius of 1.0 mm, in a direction perpendicular to the optical windows of the sample cell 1, i.e., in the "z" direction. The substantially parallel light 7 propagates in a direction parallel to the bottom of the sample cell 1, and the optical axis indicated with the dash-dotted line is located at a height of 8 mm from the bottom. In other words, the center of a circular cross section of the substantially parallel light 7 is located at a height of 8 mm from the bottom of the sample cell. A photosensor 8 for detecting a light transmitted through the sample solution sends an output signal "S", and a computer 9 analyzes the output signal S from the photosensor 8 to control the electromagnetic valve 4, the pipette 5 and the light source 6.

Next, the beam of the substantially parallel light 7 is circular in cross section, and the direction of an electric field thereof is indicated with "x" in FIG. 1. The substantially parallel light 7 is a Gaussian beam, whose optical power density on the optical axis increases to the maximum, and decreases with the distance from the optical axis at the cross section perpendicular to the propagating direction in accordance with the following formula (1):

$$I(r)=I(0)\times exp(-2r^2/w_0^2) \qquad (1)$$

where, r is a distance (m) from the optical axis at the cross section of the beam; I (r) is a power density (W/m$^2$) at a distance of r from the optical axis; I(0) is a power density (W/m$^2$) on the optical axis; and $W_0$ is a distance (m) at which the power density is $1/e^2$ of I (0), in which e is a natural logarithm.

With respect to the beam radius of the substantially parallel light 7, it is defined as; beam radius=$W_0$=1.0 mm. The power included within the radius r is obtained by integrating the power density, and approximately 86.5% of the total optical power is present within the radius $w_0$. Similarly, approximately 99.97% of the total optical power is present in the 2 $W_0$, which is two times the beam radius.

Herein, the substantially parallel light 7 is a parallel light in terms of geometrical optics, however, in actuality, it increases in the beam diameter as it propagates owing to the diffraction effect. However, there is no harm in substantially considering it as a parallel light for the beam diameter used in the present invention.

Thus, when the lowermost part of the surface 2 of the sample solution is located at the height two time the beam radius, from the optical axis of the substantially parallel light 7, that is, when d=10 mm, approximately 99.97% of the total optical power propagates through the sample solution. At this time, 5 ml or more of the sample solution is held in the sample cell 1.

On the other hand, when the lowermost part of the solution surface 2 is located at a height of 8 mm from the bottom of the sample cell 1, i.e., when d=8 mm, only about a half of the total optical power propagates through the sample solution.

The reason why the optical power propagating through the sample solution decreases in such a way when the solution surface 2 is located within the beam of the substantially parallel light 7 is that optical phenomena of reflection, refraction and diffraction concurrently occur on the solution surface thereby to diffuse the beam. For this reason, in the case where the photo detective area of the photosensor 8 perfectly coincides with the cross section of the substantially parallel light 7, when d<10 mm, the optical power reaching the photosensor 8 remarkably decreases. That is, in the case where the photo detective area of the photosensor 8 has a shape of circle having a radius of 1 mm and the center thereof coincides with the optical axis of the substantially parallel light 7, when d<is 10 mm, the optical power reaching the photosensor 8 significantly decreases owing to the diffusion of the beam. Furthermore, the diffusion of the beam is greatly influenced by the fluctuation in the level of the solution surface, and thus the optical power reaching the photosensor 8 does not stabilize.

Figure 2:
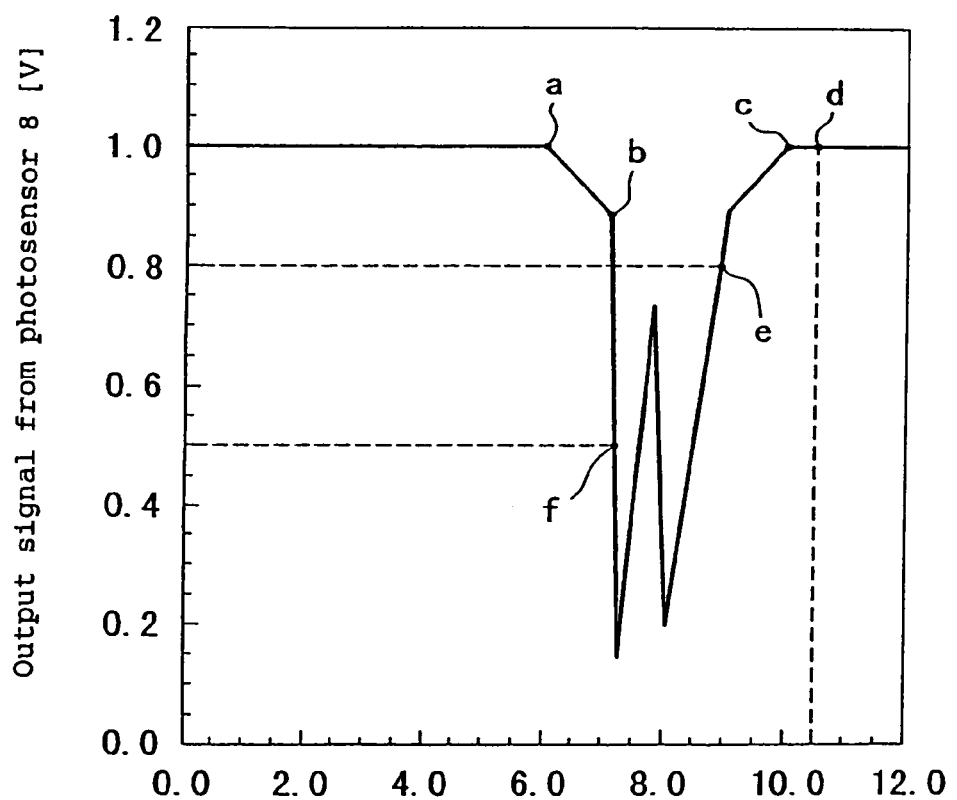
FIG. 2 is a graph showing the relation between the output signal from the photosensor and the distance from the bottom of the sample cell to the lowermost part of the solution surface or the elapsed time since the start of the dropping of the sample solution.

Next, the output signal S from the photosensor 8 was measured when a sample solution was dropped into the sample cell 1 from the funnel 3 at 0.5 ml/sec, using the apparatus for measuring an optical characteristic shown in FIG. 1. The result is shown in FIG. 2. FIG. 2 is a graph showing the relation between the output signal S from the photosensor 8 and the distance d from the bottom of the sample cell 1 to the lowermost part of the solution surface. In FIG. 2, the horizontal axis indicates the distance d from the bottom of the sample cell 1 to the lowermost part of the solution surface, and the vertical axis indicates the output signal S from the photosensor 8, wherein S was adjusted to be 1.0 V when d≧10 mm.

Herein, when the sample solution was dropped into the sample cell 1 shown in FIG. 1 at the above dropping rate, d becomes 1 mm one second after the dropping was started. Therefore, the horizontal axis of FIG. 2 also indicates the elapsed time since the start of the dropping of the sample solution. It should be noted that the sample solution was dropped into the sample cell 1 along the plane thereof without any optical window, so that the sample solution is not present in the optical path of the substantially parallel light 7 during the dropping.

As shown in FIG. 2, no influence of the sample solution is observed until d becomes approximately 6.0 mm. However, when d=6.0 to 10 mm, the output signal S significantly changes under the influence of the diffusion of the beam due to the reflection, refraction or diffraction of the substantially parallel light 7 on the solution surface 2, and the fluctuation in the level of the solution surface. Then, when d is above 10 mm, the output signal S apparently stabilizes.

As described above, the present inventor has directed his attention to the fact that the optical power density propagating through the sample solution changes owing to the positional relation between a rising solution surface and the beam axis, and as a result, has accomplished the present invention by applying such change into practical use.

Namely, the most remarkable feature of the present invention lies in verifying that the sample solution is inflowing into the sample cell, that a predetermined amount of the sample solution is held in the sample cell, and that a bubble or the like in the sample solution held in the sample cell has disappeared so that the sample solution has become stable, by measuring the output signal S and an absolute value |dS(t)/dt| of an amount of change in the output signal S over time "t" in the method for verifying an amount of a sample solution comprising the steps of: (a) detecting at least one selected from the group consisting of a transmitted light component, a scattered light component and a reflected light component of a light by a photosensor while irradiating a sample solution, which is being injected into a sample cell, with the light and (b) verifying that a predetermined amount of the sample solution is held in the sample cell based on a change in an output signal from the photosensor.

Herein, the absolute value |dS(t)/dt| of the amount of change in the output signal S over time t can be expressed as the gradient of the tangent in the graph shown in FIG. 2. Accordingly, in the present invention, the method for verifying that a predetermined amount of a sample solution is held in the sample cell based on a change in the output signal from the photosensor, for example, on the basis of the test result shown in FIG. 2, can be exemplified by the following combinations, although it is not limited thereto.

(1) An inflow of a sample solution is detected based on the fact that |dS(t)/dt| has become a predetermined value (e.g., 0.1 V/sec, which is the absolute value of the gradient of the straight line ab) or greater.

Subsequently, it is verified that a predetermined amount of the sample solution is held based on the fact that |dS(t)/dt| is maintained at a predetermined value (e.g., 0.01 V/sec) or less for a predetermined duration (e.g., 0.5 second from the point c to the point d) or longer.

(2) An inflow of a sample solution is detected based on the fact that |dS(t)/dt| has become a predetermined value (e.g., 0.1 V/sec, which is the absolute value of the gradient of the straight line ab) or greater.

Subsequently, it is verified that a predetermined amount of the sample solution is held based on the fact that |dS(t)/dt| has become a predetermined value (e.g., 0.01 V/sec) or less and S has become a predetermined value (e.g., 0.8 V at the point e) or greater.

(3) An inflow of the sample solution is detected based on the fact that S has become a predetermined value (e.g., 0.5 V at the point f) or less.

Subsequently, it is verified that a predetermined amount of the sample solution is held based on the fact that |dS(t)/dt| is maintained at a predetermined value (e.g., 0.01 V) or less for a predetermined duration (e.g., 0.5 second from the points c to the point d) or longer.

Additionally, when controlling a measurement system of an optical apparatus by using the above method for verifying an amount of a sample solution, it is preferable to carry out the optical measurement after further measuring |dS(t)/dt| to verify that a bubble has disappeared or an impurity has sedimented in the sample solution, so that the obstruction to the optical characteristic measurement has been eliminated from the optical path.

Herein, a predetermined value and a predetermined duration referred in this specification vary depending on such conditions as the type and the component of the sample solution, the type of a light to irradiate the sample solution, the type of a light to be detected (a transmitted light component, a scattered light component and/or a reflected light component). However, they can be set in advance by conducting the above experiment, which was carried out by the present inventor, for the respective types of the sample solutions under a predetermined condition, and preparing a graph showing the relation between the output signal from the photosensor and the distance from the bottom of the sample cell to the lowermost part of the solution surface (or the elapsed time since the start of the dropping of the sample solution) as shown in FIG. 2.

Then, by utilizing such a principle, the present invention also provides a method for controlling a measurement system and a method for measuring a concentration of a sample solution used in the above apparatus for measuring an optical characteristic.

Particularly, when a urine is used as the sample solution, the above principle is applicable to a method for controlling a measurement system wherein the urine discharged into a toilet bowl is received by a sample cell moved into the hollow space of the toilet bowl to be transfused from the sample cell to another sample cell, and the amount of the sample solution held in the former sample cell is verified by using the above method for verifying an amount of a sample solution.

It is also applicable to a method for controlling a measurement system wherein the urine discharged into the toilet bowl is received by the sample cell moved into the hollow space of the toilet bowl in the air, and the amount of the sample solution held in the sample cell is verified by using the above method for verifying an amount of a sample solution.

Further, it is also applicable to a method for verifying an amount of a sample solution and a method for controlling a measurement system wherein the urine discharged into the toilet bowl is received in the air by the sample cell moved into the hollow space of the toilet bowl, a transmitted light component and/or a scattered light component and/or a reflected light component of the light that irradiated the urine in the sample cell are detected by a photosensor to verify that a predetermined amount of the urine is held in the sample cell based on an output signal from the photosensor, followed by transfusing the urine to another sample cell for holding it to measure an optical characteristic thereof.

Hereinbelow, the present invention will be further described in detail by way of examples, which should not be construed as limiting the scope of the present invention.

EXAMPLE 1

In the following, Example 1 of the present invention using the apparatus for measuring an optical characteristic shown in FIG. 1 will be described more concretely.

First, while 5 ml or more of a sample solution was being injected in a funnel 3 for trapping the sample solution, a computer 9 sent an open signal to an electromagnetic valve 4, thereby starting the dropping of the sample solution trapped in the funnel 3 into a sample cell 1 at 0.5 ml/sec.

While sending this open signal, the computer 9 was set to be on standby for verifying the amount of the sample solution when an absolute value of an amount of change in an output signal S from a photosensor 8 over time $dS(t)/dt$ had become the second predetermined value or greater. For example, it was set to be on standby for verifying the amount of the sample solution when the absolute value of the amount of change in the output signal S over time $dS(t)/dt$ had become 0.1 V/sec or greater in FIG. 2.

In the state of being on standby for verifying the amount of the sample solution and sending the open signal, it was verified that a predetermined amount of the sample solution was held based on the fact that the absolute value of the amount of change in the output signal S from the photosensor 8 over time $dS(t)/dt$ was maintained at the first predetermined value or less for the first predetermined duration or longer. For example, it was verified that the predetermined amount of the sample solution was held when $dS(t)/dt$ was maintained at 0.01 V/sec or less for 0.5 second or longer, and a close signal was sent to the electromagnetic valve 4. By such controlling, d became 10.5 mm or greater, and therefore, 5.25 ml or more of the sample solution was held in the sample cell 1.

Next, from this state, the computer 9 controlled the pipette 5 to inject a predetermined amount of a reagent to be used for measuring a concentration of a specific component contained in the sample solution into the sample cell 1, thereby mixing the sample solution and the reagent while controlling or fixing the volume ratio thereof. At this time, the computer 9 analyzed the output signal S from the photosensor 8 to measure the concentration of the specific component contained in the sample solution.

According to this example, not only the amount of change in the output signal S from the photosensor 8 over time $dS(t)/dt$, but also the duration in which this amount of change was maintained was verified, which provided an effect of preventing the following erroneous operation.

Namely, at a point of inflection, at which the output signal S from the photosensor 8 that had been decreasing turned to increase (or that had been increasing turned to decrease), $dS(t)/dt$ reversed in sign of plus and minus. In other words, at this point of inflection, which generated instantaneously during the dropping of the sample solution, $dS(t)/dt$ became zero. Thus, when it was verified only that the absolute value of $dS(t)/dt$ had become the first predetermined value or less, there was the possibility that an erroneous operation would occur. This could be also held true from the fact that a plurality of points of inflection were observed in FIG. 2.

In contrast, in the present invention, not only the absolute value of the amount of change in the output signal S over time $dS(t)/dt$, but also the duration in which this amount of change was maintained was verified, and therefore, an erroneous operation due to such a plurality of points of inflection could be prevented.

As described above, the amount of the sample solution could be verified precisely when the sample solution was supplied into the sample cell, by setting the apparatus to be on standby for verifying the amount of the sample solution when the amount of change in the output signal over time $dS(t)/dt$ had become the second predetermined value or greater, and verifying that the predetermined amount of the sample solution was held when $dS(t)/dt$ was maintained at the first predetermined value or less for the first predetermined duration or longer.

In this example, since the amount of the sample solution was verified by using the substantially parallel light 7, which was a light for measuring an optical characteristic of the sample solution, and the photosensor 8 for detecting the same, it was not necessary to provide any means for verifying the amount of the sample solution separately. In other words, this example utilized the original means for measuring an optical characteristic as the means for verifying the amount of the sample solution, and therefore was effective and highly practicable. However, it was obvious that the amount of the sample solution could also be verified by providing a substantially parallel light and a photosensor aside from the light for measuring an optical characteristic, and operating them in the same manner as in this example.

Further, according to this example, the amount of the sample solution held in the sample cell could be verified, so that the volume ratio of the reagent to be injected and the sample solution could be fixed or controlled, without measuring the amount of the sample solution. Consequently, the steps for measuring an optical characteristic of the sample solution could be simplified and an erroneous operation was less likely to occur, resulting in high practicability. That is, according to the present invention, higher efficiency and laborsaving of the measurement and the test could be realized.

In this example, the substantially parallel light 7 propagated linearly in the z direction and transmitted through the sample solution thereby to reach the photosensor 8 as shown in FIG. 1. However, when the substantially parallel light 7 was made incident on the optical windows of the sample cell 1 in any angle other than that is perpendicular to the optical window, and when the respective optical windows of the sample cell were not parallel to each other, the substantially parallel light 7 was refracted before reaching the photosensor 8. Even when the substantially parallel light was refracted on the optical windows or the sample solution in this manner, the amount of the sample solution could be verified by utilizing the same mechanism described in this example, and therefore such measurement is within the scope of the present invention.

EXAMPLE 2

In the following, Example 2 of the present invention will be described in detail in the same manner as in Example 1 with reference to FIGS. 1 and 2. Although the apparatus for measuring an optical characteristic shown in FIG. 1 was used in this example, the parameter was set differently.

First, while 5 ml or more of a sample solution was being injected in the funnel 3 for trapping the sample solution, the computer 9 sent an open signal to the electromagnetic valve 4, thereby starting the dropping of the sample solution trapped in the funnel 3 into the sample cell 1 at 0.5 ml/sec. While sending this open signal, the computer 9 was set to be on standby for verifying an amount of a sample solution based on the fact that an absolute value of an amount of change in the output signal S from the photosensor 8 over time dS(t)/dt had become the second predetermined value or greater. For example, it was set to be on standby for verifying the amount of the sample solution when the absolute value of the amount of change in the output signal S over time dS(t)/dt had become 0.1 V/sec or greater in FIG. 2.

In the state of being on standby for verifying the amount of the sample solution and sending the open signal, it was verified that a predetermined amount of the sample solution was held when the absolute value of the amount of change in the output signal S from the photosensor 8 over time dS(t)/dt had become the first predetermined value or less and the magnitude of the output signal S from the photosensor 8 had become the third predetermined value or greater. For example, it was determined and verified that the predetermined amount of the sample solution was held when the absolute value of the amount of change over time dS(t)/dt had become 0.01 V/sec or less and the magnitude of the output signal S had become 0.8 V or greater, and then a close signal was sent to the electromagnetic valve 4. By such controlling, d became 10 mm or greater, and therefore, 5 ml or more of the sample solution was held in the sample cell 1.

According to this example, the amount of the sample solution was verified based on not only the absolute value of the amount of change in the output signal S from the photosensor 8 over time dS(t)/dt, but also the fact that the magnitude of the output signal S had become a predetermined value or greater, so that the following erroneous operation that might occur in Example 1 of the present invention could be prevented.

For example, when a bubble adhered to the optical window of the sample cell to be present in the optical path of the substantially parallel light 7 during the supply of the sample solution into the sample cell, the substantially parallel light 7 was scattered and reflected by the bubble, and therefore could not reach the photosensor 8. In this case, the absolute value of the amount of change in the output signal S from the photosensor 8 over time might also become 0.01 V/sec or less, resulting in an erroneous operation of mistakenly verifying that the predetermined amount of the sample solution was held.

Such an erroneous operation due to a bubble, however, could be prevented by considering the magnitude of the output signal S as a factor in the verification, in addition to the absolute value of the amount of change in the output signal S over time. Moreover, when the parameter was set as in this example, it was not necessary to verify that the absolute value of the amount of change dS(t)/dt was maintained at the second predetermined value or less for the first predetermined duration or longer, as opposed to the case where it was set as in Example 1. Thus, it became possible to shorten the time required for verifying the amount of the sample solution by the first predetermined duration, improving the efficiency of the measurement.

As described above, according to this example, the amount of the sample solution held in the sample cell could be verified with high reliability, so that the volume ratio of the reagent to be injected and the sample solution could be fixed or controlled, without measuring the amount of the sample solution. Consequently, the steps could be simplified and an erroneous operation was less likely to occur, resulting in high practicability. Further, according to the present invention, higher efficiency and laborsaving of the measurement and the test could be realized.

EXAMPLE 3

Figure 3:
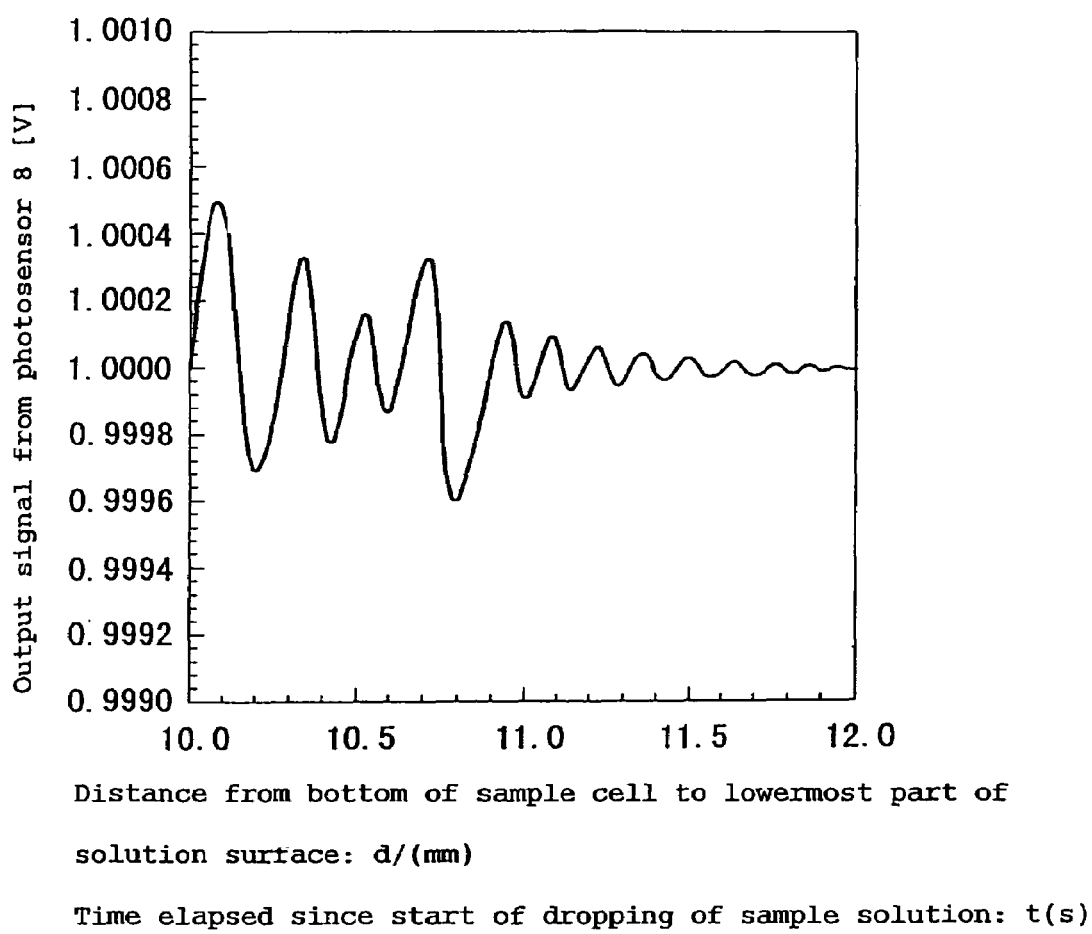
FIG. 3 is a partial enlarged view of FIG. 2 showing the value of the output signal from the photosensor 8 at around 1.0 V, when d=10 to 12.

In the following, Example 3 of the present invention will be described in detail in the same manner as in Example 1 with reference to FIGS. 1, 2 and 3. Although the apparatus for measuring an optical characteristic shown in FIG. 1 was used in this example, the parameter was set differently. Herein, the measurement of an optical characteristic of the sample solution was started upon verifying the amount of the sample solution held in the sample cell. FIG. 3 is a partial enlarged view of FIG. 2 showing the value of the output signal from the photosensor 8 at around 1.0 V, when d=10 to 12.

First, while 5 ml or more of a sample solution was being injected in the funnel 3 for trapping the sample solution, the computer 9 sent an open signal to the electromagnetic valve 4, thereby starting the dropping of the sample solution trapped in the funnel 3 into the sample cell 1 at 0.5 ml/sec. While sending this open signal, the computer 9 was set to be on standby for verifying the amount of the sample solution when the output signal S from the photosensor 8 had become the sixth predetermined value or less. For example, it was set to be on standby for verifying the amount of the sample solution when the output signal S had become 0.5 V or less in FIG. 2.

In the state of being on standby for verifying the amount of the sample solution and sending the open signal, it was verified that a predetermined amount of the sample solution was held based on the fact that the absolute value of the amount of change in the output signal S from the photosensor 8 over time dS(t)/dt was maintained at the first predetermined value or less for a predetermined duration or longer. For example, it was verified that the predetermined amount of the sample solution was held when dS(t)/dt was maintained at 0.01 V/sec or less for 0.5 second or longer, and then a close signal was sent to the electromagnetic valve 4. By such controlling, d became 10.5 mm or greater, and therefore, 5.25 ml or more of the sample solution was held in the sample cell 1.

Next, from this state, it was verified that the amount of change in the output signal S over time dS(t)/dt was maintained at the fifth predetermined value or less for the second predetermined duration or longer for starting the measurement of an optical characteristic of the sample solution. For example, the point of time, at which dS(t)/dt was maintained at 0.003 (V/sec) or less for 0.5 second or longer, was verified. In FIGS. 2 and 3, dS(t)/dt had become 0.003 (V/sec) or less when 11.1 seconds had elapsed since the start of the dropping of the sample solution, and therefore, the point of time, at which 11.6 seconds had elapsed since the start of the dropping, was verified.

When the above-described point of time was verified, an optical characteristic of the sample solution in the sample cell 1 was measured. For example, the computer 9 controlled the pipette 5 to inject a predetermined amount of a reagent to be used for measuring a concentration of a specific component contained in the sample solution into the sample cell 1, thereby fixing or controlling the volume ratio of the sample solution and the reagent. Then, the computer 9 analyzed the output signal S from the photosensor 8 to measure the concentration of the specific component contained in the sample solution.

According to this example, the amount of change in the output signal S from the photosensor 8 over time dS(t)/dt and the duration in which this amount of change was maintained were verified after verifying that the predetermined amount of the sample solution was held in the sample cell 1, and therefore, the reliability of the measurement of an optical characteristic could be enhanced because of the following reason.

Even after the inflow of the sample solution into the sample cell was suspended, a bubble or the like generating during the inflow might be present in the optical path of the substantially parallel light 7, thereby causing a fluctuation in the output signal S from the photosensor 8. This fluctuation deteriorated the reliability of the optical characteristic measurement. Therefore, the measurement was started after verifying that the predetermined amount of the sample solution was held and after further verifying that a bubble or the like had disappeared from the optical path, for example, by surfacing, and the fluctuation in the output signal had subsided by measuring the amount of change dS(t)/dt. Consequently, the reliability of the measurement could be ensured.

Namely, at a point of inflection, at which the output signal S from the photosensor 8 that had been decreasing turned to increase (or that had been increasing turned to decrease), dS(t)/dt reversed in sign of plus and minus. In other words, at this point of inflection, which generated instantaneously during the dropping of the sample solution, dS(t)/dt became zero. Thus, when it was verified only that the absolute value of dS(t)/dt had become the fifth predetermined value or less, there was the possibility that an erroneous operation would occur. This could be also held true from the fact that a plurality of points of inflection were observed in FIG. 2.

In contrast, in the present invention, not only the absolute value of the amount of change in the output signal S over time dS(t)/dt, but also the duration in which this amount of change was maintained was verified, and therefore, an erroneous operation due to such a plurality of points of inflection could be prevented.

According to this example, the amount of the sample solution held in the sample cell could be verified, so that the volume ratio of the reagent to be injected and the sample solution could be fixed or controlled, without measuring the amount of the sample solution. Further, the measurement of an optical characteristic was carried out after further verifying that an obstruction to the substantially parallel light 7, such as a bubble, was eliminated after the inflow of the sample solution was suspended, and therefore, the measurement was highly reliable. Consequently, the measurement steps could be simplified and an erroneous operation was less likely to occur, resulting in high practicability, higher efficiency and laborsaving of the measurement and the test.

EXAMPLE 4

In the following, the method for controlling a measurement system and/or the method for measuring a concentration of a sample solution will be described.

Example 4 of the present invention will be described below in detail with reference to FIGS. 4 and 5. Herein, the apparatus for measuring an optical characteristic shown in FIG. 4 was provided in a toilet bowl, and a protein concentration was examined by using a urine as a sample solution. In the apparatus for measuring an optical characteristic shown in FIG. 4, the solution surface 2, the semiconductor laser module 6, the substantially parallel light 7, the photosensor 8 and the computer 9 were the same as those shown in FIG. 1.

Figure 4:
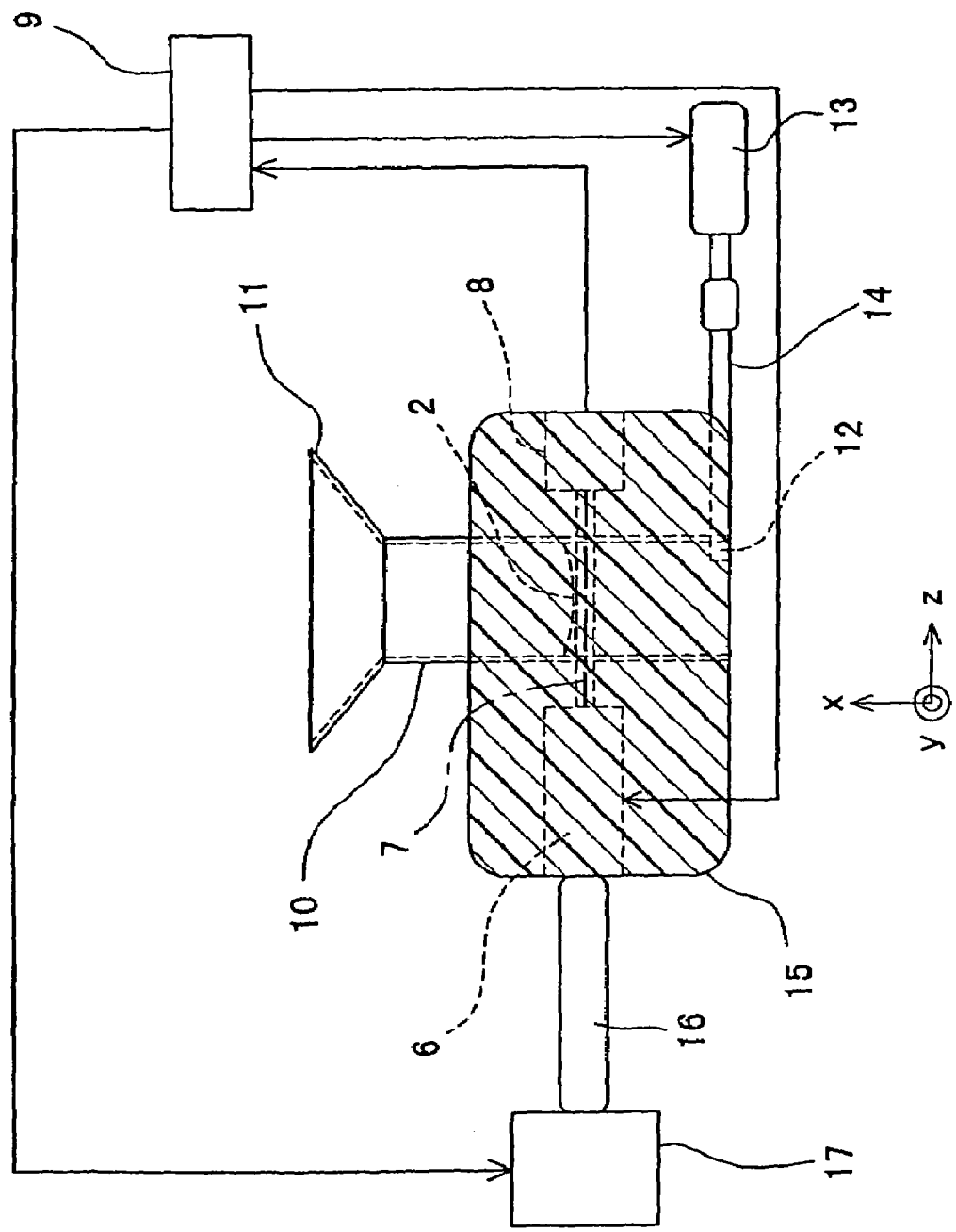
FIG. 4 is a view showing the configuration of the apparatus for measuring an optical characteristic used in Example 4 of the present invention.

The sample cell 10 shown in FIG. 4 comprised a container made of aluminum which had the shape of a rectangular solid and a funnel-like opening 11 at the top of its skeleton. A glass plate as an optical window was embedded on both ends of the optical path, so that the container allowed a light to transmit through the sample solution while holding the sample solution therein. The distance of the propagating direction of the light in the container, i.e., the distance between the optical windows was 10 mm, and the distance of a direction perpendicular to this propagating direction was 10 mm.

The optical axis of the substantially parallel light 7 was located at a height of 28 mm from the bottom of the sample cell 10. When the lowermost part of the surface 2 of the sample solution was located at the height two times the beam radius, from the optical axis of the substantially parallel light 7, that is, when the lowermost part of the solution surface 2 was located at a height of 30 mm from the bottom, approximately 99.97% of the total optical power propagated through the sample solution, as previously described. At this time, 3 ml of the sample solution was held in the sample cell 10.

Further, an inlet 12 for injecting a reagent was located at the bottom of the sample cell 10, and a pipette 13 for injecting a predetermined amount of the reagent into the sample solution held in the sample cell 10 through the inlet 12 was controlled by the computer 9. Further, an elastic tube 14 for transferring the reagent connected the pipette 13 with the inlet 12. A housing 15 is the one made of resin, which integrated the semiconductor laser module 6, the photosensor 8, the sample cell 10, the inlet 12 and the tube 14 into one piece. The housing 15 had a sealed structure, and therefore, even when the sample solution splashed on the housing, it did not reach the semiconductor laser module 6 and the photosensor 8, which were the optical components, and the optical windows on the outside of the skeleton of the sample cell 10.

Figure 5:
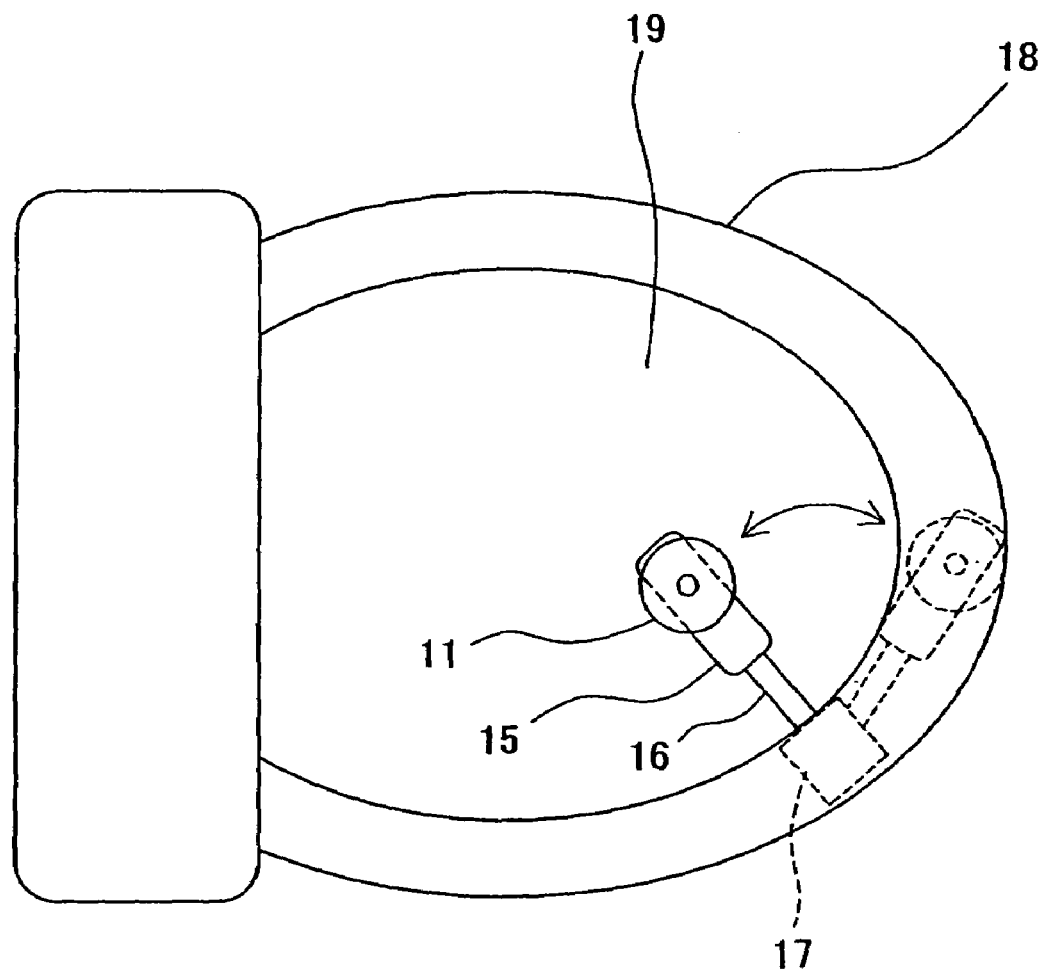
FIG. 5 is a top plan view schematically showing the toilet bowl comprising the apparatus for measuring an optical characteristic shown in FIG. 4.

Next, FIG. 5 is a top plan view schematically showing the toilet bowl comprising the apparatus for measuring an optical characteristic shown in FIG. 4. The housing 15 was connected with a shaft base 17 via a cylindrical shaft 16. As shown in FIG. 5, the shaft base 17 was installed in a Western style toilet bowl 18. The shaft base 17 was controlled by the computer 9, and it moved the shaft 16 horizontally as indicated with the arrow to move the housing 15 into a hollow space of the toilet bowl during the measurement of an optical characteristic of a discharged urine. After the measurement was completed, the housing was restored underneath the toilet seat or the like, where it had been originally located. Herein, the tube 14 has been omitted from FIG. 5. In addition, it was possible to rotate the housing 15 in a direction parallel to the sheet of the paper in FIG. 4, that is, it was possible to rotate it about the shaft 16.

The following is the operation for verifying an amount of a urine as a sample solution and further measuring a protein concentration thereof in this example.

First, according to instructions from the computer 9, the sample cell 10 was moved together with the housing 15 to the hollow space 19 of the toilet bowl 18, where the urine as the sample solution could be trapped easily. At this time, the test subject discharged a urine directly to the opening 11 of the sample cell 10. Then, it was verified that the predetermined amount of the sample solution was held in the sample cell 10 based on the output signal S from the photosensor 8 by using any one of the methods shown in Example 1 to 3. Upon the verification, the computer 9 gave instructions to the sample cell 10 to be restored, so that the sample cell 10 was restored together with the housing 15 to the initial position.

Next, the computer 9 controlled the pipette 13 to inject 3.0 ml of a sulfosalicylic acid reagent (a reagent obtained by dissolving sodium sulfate in an aqueous solution of 2-hydroxy-5-sulfobenzoic acid) into the sample cell 10. As a result, it was possible to mix the sample solution and the reagent at the volume ratio of 1:1. At this time, the computer 9 analyzed the output signal S from the photosensor 8 to measure the concentration of the sample solution.

Subsequently, according to instructions from the computer 9, the housing 15 was inclined by using the shaft 16 as an axis to discharge the sample solution held in the sample cell 10 into the toilet bowl 18 through the funnel-like opening 11 at the top. Then, the sample cell 10, the opening 11, the housing 15 and the shaft 16 were washed. The washing was carried out, for example, by jetting a cleaning solution like a shower.

As described above, according to this example, the amount of the sample solution held in the sample cell could be verified, so that the volume ratio of the reagent to be injected and the sample solution could be fixed or controlled, without measuring the amount of the sample solution. Further, the whole of the housing 15, which integrated the light source, the photosensor and the sample cell into one piece, was easily moved to the right place for trapping the sample solution, resulting in efficiency. An optical alignment error of the optical axis and the like were less likely to occur, as compared with the case where only the sample cell was moved at this step. Moreover, since the housing 15 had a sealed structure, there was no danger that the sample solution and the like adhered to the respective optical components to obstruct the measurement. In particular, when the sample solution was a urine, the sample cell 10 could be moved into the hollow space 19 of the toilet bowl 18 together with the housing 15 to trap a predetermined amount of the urine in the air. Consequently, urine could be tested easily. Furthermore, an erroneous operation was less likely to occur and the operational stability was improved, resulting in a high practicability. That is, according to the present invention, higher efficiency and laborsaving of the measurement and the test could be realized. Moreover, it was not necessary for the user to treat the urine directly, promoting the widespread use of the test at home.

In the present Example, after verifying the amount of the sample solution, the sample cell 10 was restored to the initial position, where it had been located before being moved into the hollow space 19, and an optical characteristic was measured thereafter. However, after verifying the amount of the sample solution, the sample cell 10 could be restored to the initial position described above, after suspending the inflow of the sample solution and measuring the optical characteristic.

Further, in this example, the sample cell 10 was washed after it was inclined to discharge the sample solution. However, the washing of the sample cell and the discharging of the sample solution could be carried out simultaneously by injecting the cleaning solution from the inlet 12 for the reagent into the sample cell while making the sample solution overflowed from the opening 11, without inclining the sample cell 10. That is, the discharging and the washing might be carried out while replacing the sample solution with the cleaning solution;

EXAMPLE 5

In the following, Example 5 of the present invention will be described in detail with reference to FIGS. 5 and 6. In the apparatus for measuring an optical characteristic shown in FIG. 6, the solution surface 2, the semiconductor laser module 6, the substantially parallel light 7, the photosensor 8 and the computer 9, the sample cell 10, the opening 11, the housing 15, the shaft 16 and the shaft base 17 were the same as those shown in FIG. 5 of Example 4. However, in this example, the substantially parallel light 7 was used only for verifying an amount of the sample solution, but not for measuring an optical characteristic of the sample solution. Further, the sample cell 10 was used as a container for trapping the sample solution, but not as a sample cell for holding the sample solution in the optical characteristic measurement.

Figure 6:
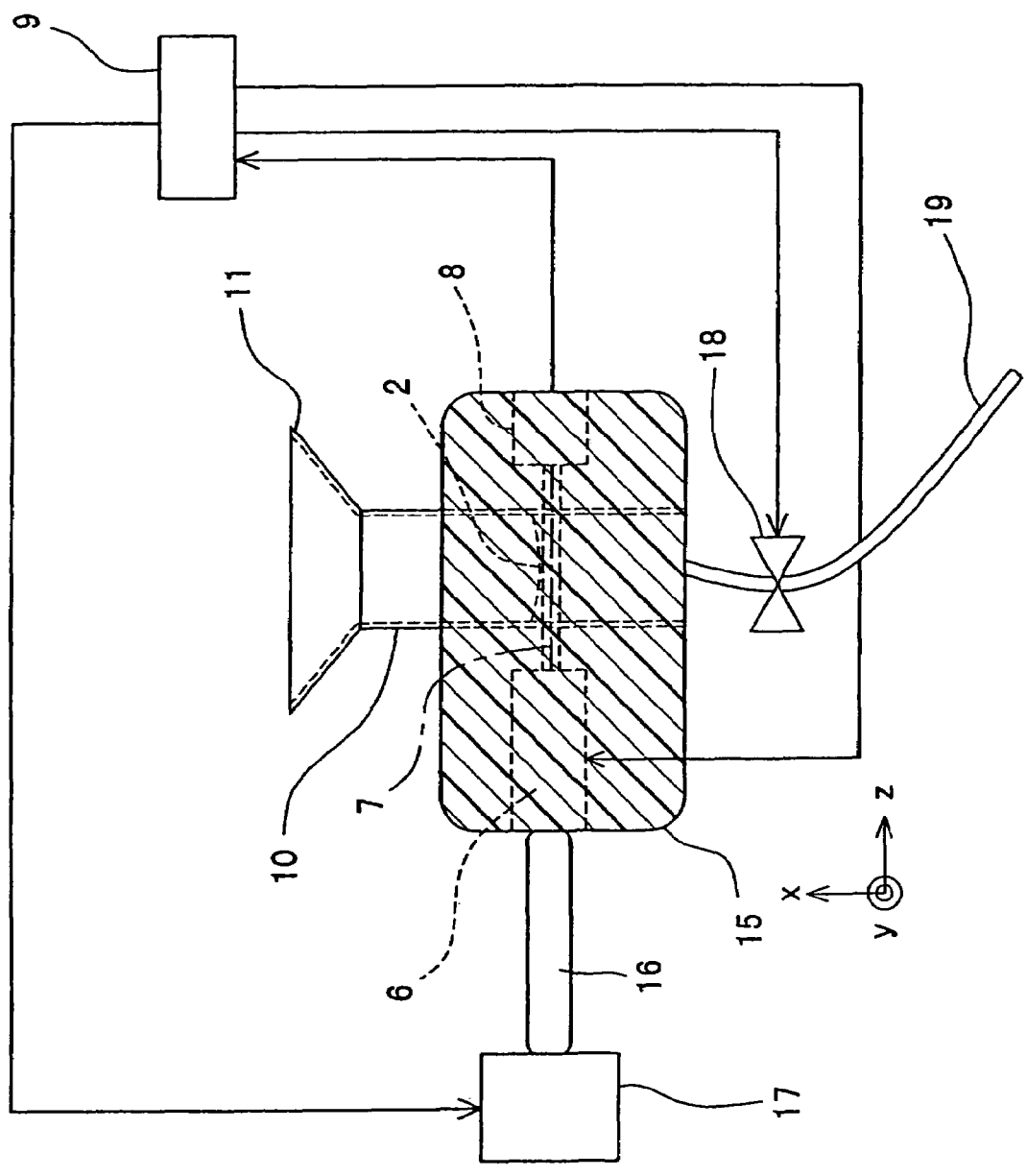
FIG. 6 is a view showing the configuration of the apparatus for measuring an optical characteristic used in Example 5 of the present invention.

In the apparatus for measuring an optical characteristic shown in FIG. 6, the electromagnetic valve 18 was controlled by the computer 9. A tube 19 transferred the sample solution trapped in the sample cell 10 to another sample cell for measuring an optical characteristic. Further, as in Example 4, the housing 15 was connected with the shaft base 17 via the cylindrical shaft 16.

As shown in FIG. 5, the shaft base 17 was installed in a Western style toilet bowl 18. The shaft base 17 was controlled by the computer 9, and it moved the shaft 16 horizontally as indicated with the arrow to move the sample cell together with the housing 15 into the hollow space 19 of the toilet bowl when measuring an optical characteristic of the discharged urine. Then, after the measurement was completed, the sample cell 10 was restored underneath the toilet seat or the like, where it had been originally located. Alternatively, it was possible to rotate the sample cell 10 together with the housing 15 in a direction parallel to the sheet of the paper in FIG. 4, that is, it was possible to rotate it about the shaft 16.

The following is the operation for verifying an amount of a urine as a sample solution and further measuring a protein concentration thereof in this example.

First, according to instructions from the computer 9, the sample cell 10 was moved together with the housing 15 to the hollow space 19 of the toilet bowl 18, where the urine as the sample solution could be trapped easily. At this time, the test subject discharged the urine directly to the opening 11 of the sample cell 10. Then, it was verified that the predetermined amount of the sample solution was held in the container 10 based upon the output signal S from the photosensor 8 by using any one of the methods shown in Examples 1 to 3.

Upon the verification, the computer 9 instructed the electromagnetic valve 18, thereby transfusing the sample solution via the tube 19 to another sample cell for measuring the sample solution. By conducting such transfusion on several separate occasions, concentrations of a plurality of specific substances could be measured. That is, the sample solution was transfused to the sample cell first for measuring the sample solution and a reagent was mixed with the sample solution to measure the concentration of a certain specific substance, followed by discharging the sample solution. Subsequently, the sample solution was transfused from the sample cell 10 to the sample cell for measuring the sample solution again, and another reagent was mixed with the sample solution to measure a concentration of another specific substance contained in the sample solution.

Upon completion of the series of measurements, the computer 9 gave instructions so that the housing 15 was inclined by using the shaft 16 as an axis to discharge the remaining sample solution in the sample cell 10 into the toilet bowl 18 through the funnel-like opening 11 at the top. Then, the sample cell 10, the opening 11, the housing 15 and the shaft 16 were washed.

As described above, according to this example, a predetermined amount of the urine could be trapped in the air by the container moved into the hollow space of the toilet bowl. In addition, the urine could be tested by transfusing the urine to the sample cell for holding the urine during the optical characteristic measurement of the urine. At this time, by conducting such transfusion on several separate occasions, a plurality of measurements could be conducted. Consequently, a plurality of test items could be examined easily. Further, an erroneous operation was less likely to occur and the operational stability was improved, resulting in high practicability. That is, according to the present invention, higher efficiency and laborsaving of the measurement and the test could be realized. Moreover, it was not necessary for the user to treat the urine directly, promoting the widespread use of the test at home.

EXAMPLE 6

In the following, Example 6 will be described in detail with reference to FIGS. 7 to 9. In this example, a method for verifying an amount of a sample solution and a method for controlling a measurement system and/or a concentration of a sample solution of the present invention were used for measuring an optically active substance and a protein concentration in the sample solution.

Figure 7:
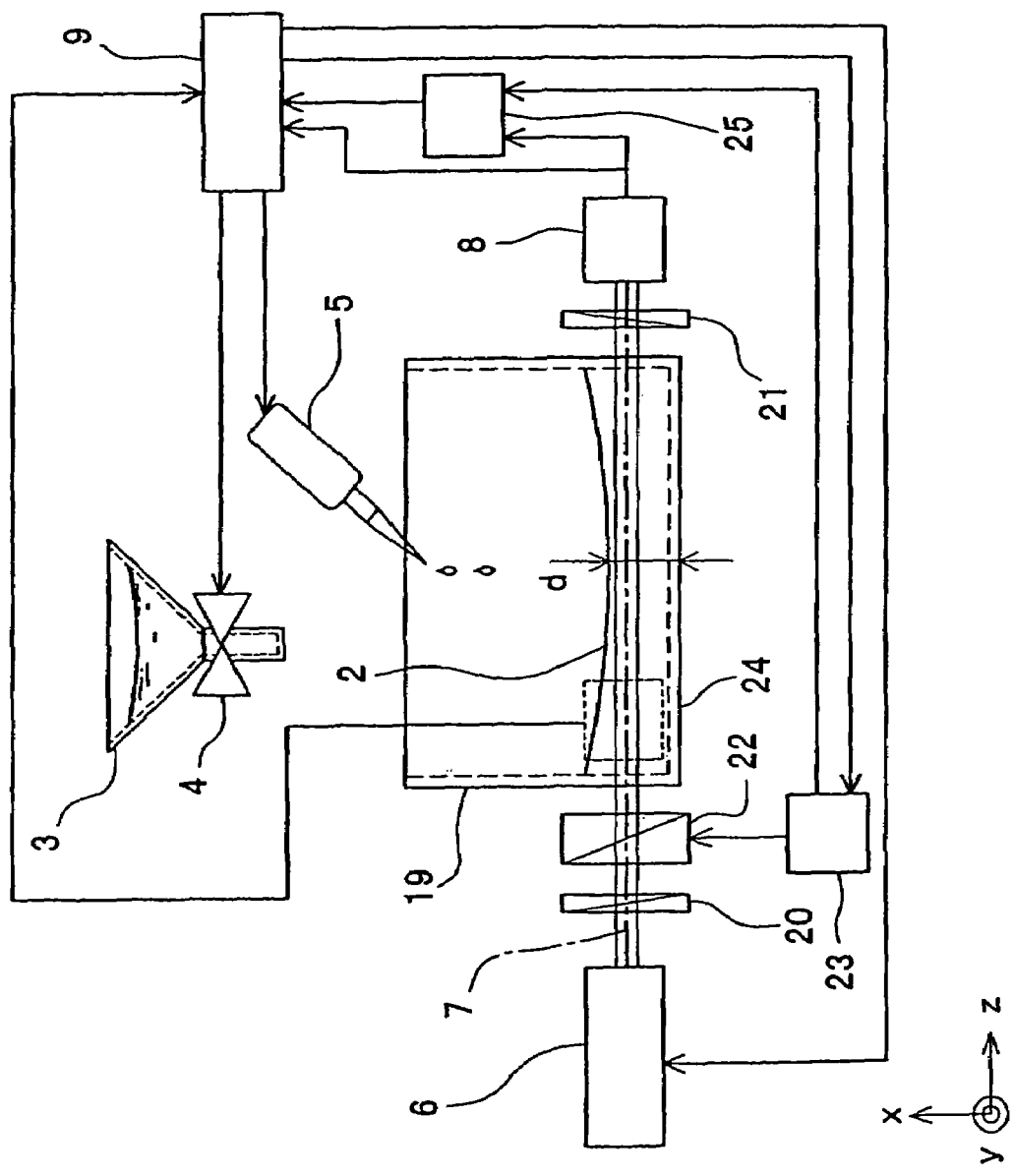
FIG. 7 is a view showing the configuration of the apparatus for measuring an optical characteristic used in Examples 6 and 7 of the present invention.

FIG. 7 is a view showing the configuration of the apparatus for measuring an optical characteristic used in this example. FIG. 8 is a top plan view schematically showing the apparatus for measuring an optical characteristic shown in FIG. 7.

In the apparatus for measuring an optical characteristic shown in FIG. 7, the solution surface 2, the funnel 3, the electromagnetic valve 4, the pipette 5, the semiconductor laser module 6, the substantially parallel light 7, the photosensor 8 and the computer 9 were the same as those shown in FIG. 1. A sample cell 19 was basically the same as the sample cell 1 of FIG. 1, except that an optical window for introducing a scattered light, which arose when the substantially parallel light 7 propagated through the sample solution, to the outside of the sample cell was provided on the sidewall thereof in the direction of the short axis, that is, a direction perpendicular to the substantially parallel light 7 (not shown). In other words, as shown in FIG. 8, the optical window was provided so that a scattered light 26, which arose in the sample solution and propagated in the "–y" direction, could be detected by a photosensor 24.

A polarizer 20 transmitted only a polarization component in the "x" direction shown in FIG. 7. An analyzer 21 was arranged so as to transmit only a polarization component in the y direction shown in FIG. 8. In addition, by using an optical Faraday effect, an optical Faraday modulator 22 modulated and controlled the polarization direction, which was regulated in the x direction by the polarizer 20. A driver 23 controlled the optical Faraday modulator 22, while supplying a modulation signal to a lock-in amplifier 25. The photosensor 8 detected the substantially parallel light 7, which had transmitted through the analyzer 21. The lock-in amplifier 25 performed a phase sensitive detection on the output signal from the photosensor 8 using the modulated signal of the optical Faraday modulator 22 as a reference signal.

In this example, the computer 9 supplied a control current signal to the driver 23 to make the output signal from the lock-in amplifier 25 zero, thereby also playing a role in measuring an angle of rotation of the sample solution. In this example, the computer 9 passed a modulation current having a frequency of 1.3 KHz to the driver 23. By controlling the modulation current, the modulation signal (control current signal or compensation control current), at which the output signal from the lock-in amplifier 25 was cancelled to become zero, was found to calculate the angle of rotation.

The photosensor 24 for detecting the scattered light 26 measured the turbidity, when the computer 9 analyzed this output signal to opacify the sample solution by mixing thereto a reagent through the pipette 5. In general, the intensity of the scattered light 26, which arose in the sample solution before the mixing of the reagent, was extremely small and therefore was not detected by the photosensor 24.

In this example, as in Example 1, when the lowermost part of the surface 2 of the sample solution was located at the height two times the beam radius, from the optical axis of the substantially parallel light 7, that is, when d=10 mm, approximately 99.97% of the total optical power propagated through the sample solution. At this time, 5 ml or more of the sample solution of was held in the sample cell 19.

Herein, when the lowermost part of the solution surface 2 was located at a height of 8 mm from the bottom of the sample cell 19, that is, when d=8 mm, only about a half of the total optical power propagated through the sample solution. When the solution surface 2 was located within the beam of the substantially parallel light 7, the optical phenomena of reflection, refraction and diffraction concurrently occur on the solution surface, thereby diffusing the beam.

Then, the optical power that was sufficiently greater than the intensity of the scattered light, which had arisen in the sample solution before the mixing of the reagent, reached the photosensor 24 and significantly fluctuated. Further, under the influence of the diffusion of the beam and the fluctuation in the level of the solution surface, the optical power reaching the photosensor 24 did not stabilize. Moreover, as in Example 1, the optical power, which had propagated through the analyzer 21 to reach the photosensor 8, was also influenced by the diffusion of the beam.

Figure 8:
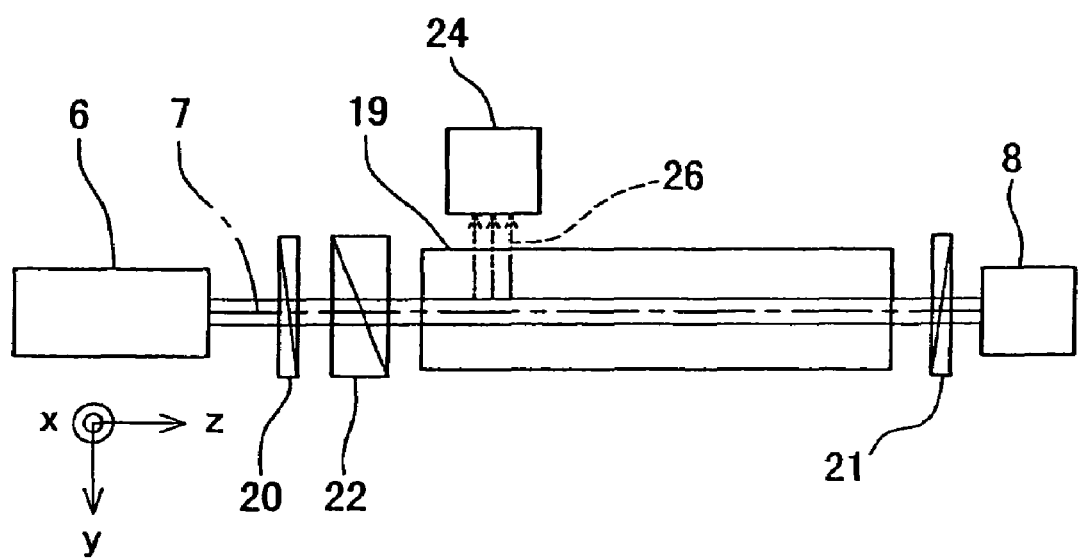
FIG. 8 is a top plan view schematically showing the apparatus for measuring an optical characteristic shown in FIG. 7.

FIG. 9 shows an example of the output signal S from the photosensor 24 when the sample solution was dropped into the sample cell 19 through the funnel 3 at 0.5 ml/sec using the apparatus for measuring an optical characteristic shown in FIGS. 7 and 8. In FIG. 9, the horizontal axis indicated the distance d from the bottom of the sample cell 19 to the lowermost part of the solution surface, and the vertical axis indicated the output signal S from the photosensor 24, whose maximum value was adjusted to be 1.0 V in the process of supplying the sample solution. Herein, when the sample solution was dropped into the sample cell 19 of this example at the above dropping rate, d became 1 mm one second after the dropping was started. Therefore, the horizontal axis of FIG. 9 also indicated the elapsed time since the start of the dropping of the sample solution. It should be noted that the sample solution was dropped into the sample cell 19 along the plane thereof without any optical window, which window was provided at three places of the sample cell, and therefore, the sample solution was not present in the optical paths of the substantially parallel light 7 and the scattered light 26 during the dropping.

As shown in FIG. 9, until d was approximately 6.0 mm, the output signal S was zero and no influence of the sample solution was observed. However, when d=6.0 to 10 mm, the output signal S significantly changed under the influence of the diffusion of the beam due to reflection, refraction or diffraction of the substantially parallel light 7 on the solution surface 2, and the fluctuation in the level of the solution surface. Then, when d was above 10 mm, the output signal S was apparently zero and stabilized.

Based on such phenomena, any one of Examples 1 to 3 above might be used as the method for verifying an amount of a sample solution. However, the method herein was set as follows.

First, while 5 ml or more of a sample solution was being injected in the funnel 3 for trapping the sample solution, the computer 9 sent an open signal to the electromagnetic valve 4, thereby starting the dropping of the sample solution trapped in the funnel 3 into the sample cell 19 at 0.5 ml/sec. While sending this open signal, the computer 9 was set to be on standby for verifying an amount of a sample solution based on the fact that an absolute value of an amount of change in an output signal S from the photosensor 24 over time dS(t)/dt had become the second predetermined value or greater. For example, the computer 9 was set to be on standby for verifying the amount of the sample solution based on the fact that the absolute value of an amount of change in the output signal S over time dS(t)/dt had become 0.1 V/sec or greater in FIG. 9.

In the state of being on standby for verifying the amount of the sample solution and sending the open signal, it was verified that a predetermined amount of the sample solution was held based on the fact that the absolute value of the amount of change in the output signal S from the photosensor 24 over time dS(t)/dt was maintained at the first predetermined value or less for the first predetermined duration or longer. For example, it was verified that the predetermined amount of the sample solution was held when dS(t)/dt was maintained at 0.01 V/sec or less for 0.5 second or longer, and then a close signal was sent to the electromagnetic valve 4. By such controlling, d became 10.5 mm or greater, and therefore, 5.25 ml or more of the sample solution was held in the sample cell 19.

The following is the operation for measuring a glucose concentration, i.e., a urine sugar value, and a urine protein concentration using a urine as the sample solution in this state.

First, the computer 9 started to operate the driver 23 to measure an angle of rotation of the sample solution. Next, the computer 9 suspended the operation of the coil driver 23, and controlled the pipette 5 to drop a sulfosalicylic acid reagent (a reagent obtained by dissolving sodium sulfate in an aqueous solution of 2-hydroxy-5-sulfobenzoic acid) into the sample cell 19. By dropping the reagent into the sample cell 19 in this state, the volume ratio of the sample solution and the reagent could be fixed or controlled. The protein concentration was measured by analyzing the change in the output signal from the photosensor 24 that occurred after the dropping of the reagent. In this measurement of the protein concentration, the concentration was calculated by comparing the measured concentration with the calibration line, which had been previously prepared.

In the following, a urine having a urine sugar value of 100 (mg/dl) and a urine protein concentration of 15 (mg/dl) was measured as the sample solution.

As a result of the measurement, the angle of rotation was approximately 0.017°. Herein, the specific angle of rotation of glucose at this wavelength (670 nm) was approximately 40° (deg/cm·dl/kg). Therefore, on the assumption that the angle of rotation was entirely due to glucose, the glucose concentration, i.e., the urine sugar value was 85 (mg/dl). Herein, the specific angle of rotation of protein was approximately −40° (deg/cm·dl/kg). In other words, it was opposite in sign and the same in the absolute value as compared with that of glucose. Accordingly, the glucose concentration was calculated at 85 (mg/dl) by subtracting 15 from 100. Therefore, it was confirmed that the measurement was carried out accurately.

When the protein concentration was measured by mixing the reagent with the sample solution and comparing the output signal from the photosensor 24 with the calibration line which had been previously prepared, the protein concentration was calculated at 15 (mg/dl). Therefore, it was confirmed that the measurement was carried out accurately.

According to this example, not only the amount of change in the output signal S from the photosensor 24 over time dS(t)/dt, but also the duration in which this amount of change was maintained was verified, and therefore, the following erroneous operation could be prevented.

At a point of inflection, at which the output signal S from the photosensor 28 that had been decreasing turned to increase (or that had been increasing turned to decrease), dS(t)/dt reversed in sign of plus and minus. Therefore, at this point of inflection, which generated instantaneously, dS(t)/dt became zero. Thus, when it was verified only that an absolute value of dS(t)/dt had become the first predetermined value or less, an erroneous operation occurred. However, by verifying not only the absolute value of the amount of change in the output signal S over time dS(t)/dt, but also the duration in which this amount of change was maintained, an erroneous operation due to such a plurality of points of inflection could be prevented.

As described above, the amount of the sample solution could be verified when the sample solution was supplied into the sample cell, by setting the apparatus to be on standby for verifying the amount of the sample solution based on the fact that an amount of change in the output signal S over time dS(t)/dt had become the second predetermined value or greater, and verifying that a predetermined amount of the sample solution was held when dS(t)/dt was maintained at the first predetermined value or less for the first predetermined duration or longer.

In this example, since the substantially parallel light 7, which was a light for measuring an optical characteristic of the sample solution, and the photosensor 24 for detecting the same were used for verifying the amount of the sample solution, it was not necessary to provide any means for verifying the amount of the sample solution separately. In other words, this example utilized the original means for measuring an optical characteristic as the means for verifying the amount of the sample solution, and therefore was effective and highly practicable. However, it was obvious that the amount of the sample solution could also be verified by providing a substantially parallel light and a photosensor aside from the light for measuring an optical characteristic of the sample solution, and operating them in the same manner as in this example.

Further, according to this example, the amount of the sample solution held in the sample cell could be verified, so that the volume ratio of the reagent to be injected and the sample solution could be fixed or controlled, without measuring the amount of the sample solution. Consequently, the steps could be simplified and an erroneous operation was less likely to occur, resulting in high practicability. Further, higher efficiency and laborsaving of the measurement and the test could be realized.

Further, according to this example, a protein concentration of the sample solution could be determined by measuring the angle of rotation thereof. That is, the protein concentration could be determined by measuring the angle of spontaneous rotation and the concentration of a spontaneous optically active substance based upon the angle of magnetorotation at which the angle of rotation due to the spontaneous optically active substance in the sample solution was identical with the angle of rotation due to a Faraday effect (magnetorotation) and mixing a reagent with the sample solution. This example was particularly practicable when the sample solution was a urine. In this example, the reagent was mixed with the sample solution after the measurement of the angle of rotation, and therefore, both the angle of rotation and the protein concentration could be measured. The reason is that the mixing of the reagent might cause the protein component to coagulate or color, preventing a light from transmitting through the sample solution. Additionally, the reagent might cause the protein to denature to change the angle of rotation thereof.

Herein, in this example, the amount of the sample solution was verified based on the output signal S from the photosensor 24 for detecting a scattered light. However, the output signal S from the photosensor 8 for measuring an angle of rotation could also be used. The substantially parallel light 7, which had transmitted through the analyzer 21, was made incident on the photosensor 8. However, when the optical Faraday modulator 22 was not in operation, the polarizer 20 and the analyzer 21 were arranged in a so-called crossed Nicol states, and therefore it was a light component, which had leaked from the substantially parallel light 7, that transmitted through the analyzer 21. This light component was significantly less compared with the transmitted light component in Example 1 (approximately $10^{-5}$ or less). However, the apparatus could be operated in the same manner as in Example 1 by adjusting S to be 1 (V) when $d \geq 10$ mm.

Even when the optical Faraday modulator 22 was in operation, the apparatus could be operated in the same manner as in Example 1 by adjusting S to be 1 (V) when $d \geq 10$ mm, so long as the rotating angle of the polarization direction was fixed.

It should be noted that the lights detected by the photosensor 24 included the ones that had been reflected on the respective solution surfaces (the surface of a drop-like sample solution as well as the solution surface 2), in addition to the ones that had arisen in the sample solution. Even on the assumption that the lights to be made incident on the photosensor 24 were only the reflected light components above, the output signal from the photosensor 24 fluctuated greatly when the solution surface 2 was within the beam of the substantially parallel light 7, and it became stable when a predetermined amount of the sample solution was held, as shown in FIG. 9. Therefore, even if only the reflected light components were detected, the method of this example could be conducted. When the amount of the sample solution was verified in this fashion, it was not necessary to distinguish between these reflected light components and the scattered light component, and therefore, all of them were described as the scattered light 26 in this example.

EXAMPLE 7

This example relates to the method for verifying an amount of a sample solution and the start of the measurement thereof using the apparatus for measuring an optical characteristic shown in FIGS. 7 and 8 of Example 6 in the following manner. This example will be described with reference to FIGS. 9 and 10. FIG. 10 is a partial enlarged view of FIG. 9 showing the value of the output signal S from the photosensor 24 at around 0 V, when d=10 to 12.

In this example, as in Example 6, while the sample solution was being dropped into the sample cell 19, the amount of the sample solution was verified based on the fact that an amount of change in the output signal S from the photosensor 24 over time dS(t)/dt had become the second predetermined value or less and that the output signal S from the photosensor 24 had become the fourth predetermined value or less. For example, it was verified that the predetermined amount of the sample solution was held when dS(t)/dt had become 0.01 V/sec or less and S had become 0.01 V or less, and then a close signal was sent to the electromagnetic valve 4. By such controlling, d became 10 mm or greater, and therefore, 5 ml or more of the sample solution was held in the sample cell 19.

As such, according to this example, the amount of the sample solution was verified based on not only the absolute value of the amount of change in the output signal S from the photosensor 24 over time, but also the fact that the magnitude of the output signal S had become a predetermined value or less, so that the following erroneous operation that might occur in Example 6 could be prevented.

For example, when a bubble adhered to an optical window of the sample cell to be present in the optical path of the substantially parallel light 7 during the supply of the sample solution into the sample cell, the substantially parallel light 7 was scattered and reflected by the bubble, and therefore could not reach the photosensor 24. Even in this case, the absolute value of the amount of change in the output signal S from the photosensor 24 over time might become 0.01 V/sec or less, resulting in an erroneous operation of mistakenly verifying that the predetermined amount of the sample solution was held. Such an erroneous operation due to a bubble, however, could be prevented by considering the magnitude of the output signal S as a factor in the verification, in addition to the absolute value of the amount of change in the output signal S over time.

Next, from this state, it was verified that the amount of change in the output signal S over time dS(t)/dt was maintained at the fifth predetermined value or less for the second predetermined duration or longer for starting the measurement of an optical characteristic of the sample solution. For example, the point of time, at which dS(t)/dt was maintained at 0.0015 (V/sec) or less for 0.5 second or longer, was verified. In FIGS. 9 and 10, dS(t)/dt had become 0.0015 (V/sec) or less when 11.1 seconds had elapsed since the start of the dropping of the sample solution, and therefore the point of time, at which 11.6 seconds had elapsed since the start of the dropping, was verified.

Upon this verification, an optical characteristic of the sample solution in the sample cell 19 was measured in the same manner as in Example 6.

According to this example, the amount of change in the output signal S from the photosensor 24 over time dS(t)/dt and the duration in which this amount of change was maintained were verified after verifying that the predetermined amount of the sample solution was held in the sample cell 19, and therefore, the reliability of the measurement of an optical characteristic could be enhanced because of the following reason.

Even after the inflow of sample solution into the sample cell 19 was suspended, a bubble or the like generated during the inflow might be present in the optical path of the substantially parallel light 7, thereby causing a fluctuation in the output signal S from the photosensor 24. This fluctuation deteriorated the reliability of the optical characteristic measurement. Therefore, the measurement was started after a bubble disappeared from the optical path, for example, by surfacing, and the fluctuation in the output signal had subsided. In other words, the measurement was started after the amount of change over time dS(t)/dt was maintained at the fifth predetermined value or less for the second predetermined duration or longer. Consequently, the reliability of the measurement could be ensured.

As described above, according to this example, the amount of the sample solution held in the sample cell could be verified, so that the volume ratio of the reagent to be injected and the sample solution could be fixed or controlled, without measuring the amount of the sample solution. Furthermore, the measurement of an optical characteristic was carried out after verifying that an obstruction in the substantially parallel light 7, such as a bubble, was eliminated after the inflow of the sample solution was suspended, and thus the measurement was highly reliable. Consequently, the steps could be simplified and an erroneous operation was less likely to occur, resulting in high practicability. Further, higher efficiency and laborsaving of the measurement and the test could be realized.

Hereinbelow, the above characteristic of the present invention will be described in detail.

When calculating the amount of change in the output signal S from the photosensor 24 over time dS(t)/dt in real time, it was necessary to either configure a differentiation circuit in an analog fashion or to perform a digital calculation. The differentiation time constant of the circuit in the former case, and the sampling interval in the latter case must be sufficiently less than the first predetermined duration or the second predetermined duration, or otherwise, the response speed would decrease to prolong the time required for verification after the predetermined amount of the sample solution was held. As a result, the time required for the entire measuring process was prolonged, resulting in reduced efficiency of the measurement. In each of Examples of the present invention, there was described the case where the differentiation time constant or the sampling interval was sufficiently less than the first predetermined duration and the second predetermined duration.

As described above, according to the present invention, the amount of the sample solution held in the sample cell can be verified, so that the volume ratio of the reagent to be injected and the sample solution can be fixed or controlled without measuring the amount of the sample solution. Consequently, the steps can be simplified and an erroneous operation is less likely to occur, resulting in high practicability. Further, higher efficiency and laborsaving of the measurement and the test can be realized.

Moreover, the whole of the housing 15, which integrates the light source, the photosensor and the sample cell into one piece, is moved to the right place for trapping the sample solution, resulting in efficiency. At this step, unlike the case where only the sample cell is moved, an optical alignment error of the optical axis or the like does not occur. Moreover, since the housing 15 has a sealed structure, there is no danger that the sample solution and the like adhere to the respective optical components to obstruct the measurement. In particular, when the sample solution is a urine, the sample cell 10 can be moved together with the housing 15 into the hollow space 19 of the toilet bowl 18 to trap a predetermined amount of the urine in the air. Consequently, the urine can be tested easily, an erroneous operation is less likely to occur and the operational stability can be improved. This provides a great practicability, and a higher efficiency and laborsaving of the measurement and the test can be realized. Further, it is not necessary for the user to treat the urine directly, promoting the widespread use of the test at home.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

The invention claimed is:

1. A method for controlling a measurement system comprising the steps of:
    (a) detecting at least one selected from the group consisting of a transmitted light component, a scattered light component and a reflected light component of a light which is traversed by a rising surface of a sample solution being injected into a sample cell, and outputting an output signal corresponding to the detection;
    (b) verifying that a predetermined amount of said sample solution is held in said sample cell based on a change in the output signal; and then
    (c) measuring an optical characteristic of the sample solution,
    wherein step (b) is performed based on the rate at which the output signal changes over time, and
    wherein said light in the step (a) is also used for measuring said optical characteristic in the step (c).

2. The method for controlling a measurement system in accordance with claim 1, further comprising a step of:
    verifying that said sample solution has become stable based on the fact that said absolute value of said amount of change in said output signal is maintained at or less than a predetermined value for a predetermined duration or longer, after the step (b) and before the step (c).

3. The method for controlling a measurement system in accordance with claim 1, further comprising the steps of:
    (d) discharging said sample solution from said sample cell after the step (c); and then
    (e) washing said sample cell.

4. The method for controlling a measurement system in accordance with claim 3, wherein the steps (d) and (e) are conducted simultaneously by replacing said sample solution in said sample cell with a cleaning solution.

5. The method for controlling a measurement system in accordance with claim 1, wherein said sample solution is a urine, the steps (a) to (c) are conducted after said sample cell installed in a position closed to a side wall of a toilet bowl is moved into a hollow space of said toilet bowl.

6. The method for controlling a measurement system in accordance with claim 1, wherein said sample solution is a urine, the steps (a) and (b) are conducted after said sample cell installed in a position closed to a side wall of a toilet bowl is moved into a hollow space of said toilet bowl, and step (c) is conducted after said sample cell is restored to the initial position.

7. The method for controlling a measurement system in accordance with claim 5, wherein a urine and/or a cleaning solution is discharged into a toilet bowl.

8. The method for controlling a measurement system in accordance with claim 1, wherein step (b) is a step of verifying that said predetermined amount of said sample solution is held in said sample cell based on the fact that an absolute value of an amount of change in said output signal over time is maintained at or less than a first predetermined value for a first predetermined duration or longer.

9. A method for controlling a measurement system comprising the steps of:
   (a) detecting at least one selected from the group consisting of a transmitted light component, a scattered light component and a reflected light component of a light which is traversed by a rising surface of a sample solution being injected into a sample cell, and outputting an output signal corresponding to the detection;
   (b) verifying that a predetermined amount of said sample solution is held in said sample cell based on a change in the output signal; and then
   (c) measuring an optical characteristic of the sample solution,
   wherein step (b) is performed based on the rate at which the output signal changes over time, and
   where said sample solution is transfused from said cell to another sample cell after the step (b), and step (c) is conducted thereafter.

10. A method for controlling a measurement system comprising the steps of:
   (a) detecting at least one selected from the group consisting of a transmitted light component, a scattered light component and a reflected light component of a light which is traversed by a rising surface of a sample solution being injected into a sample cell, and outputting an output signal corresponding to the detection;
   (b) verifying that a predetermined amount of said sample solution is held in said sample cell based on a change in the output signal; and then
   (c) measuring an optical characteristic of the sample solution,
   wherein step (b) is performed based on the rate at which the output signal changes over time, and
   wherein the step (c) is a step of detecting a light, which has been transmitted through said sample solution and an analyzer, by a photosensor to measure an angle of rotation of said sample solution, using an output signal from said photosensor as a transmitted light component.

* * * * *